United States Patent [19]

Jackson

[11] Patent Number: 4,659,700

[45] Date of Patent: Apr. 21, 1987

[54] CHITOSAN-GLYCEROL-WATER GEL

[75] Inventor: David S. Jackson, Princeton, N.J.

[73] Assignee: Johnson & Johnson Products, Inc., New Brunswick, N.J.

[21] Appl. No.: 585,714

[22] Filed: Mar. 2, 1984

[51] Int. Cl.$^4$ .......................................... A61K 31/725
[52] U.S. Cl. .................................... 514/55; 536/20
[58] Field of Search ............... 424/180, DIG. 13; 536/20; 514/55

[56] References Cited

U.S. PATENT DOCUMENTS

| | | | |
|---|---|---|---|
| 2,623,909 | 12/1952 | Robeson et al. | 568/867 |
| 3,155,575 | 11/1964 | Docgi et al. | 514/55 |
| 3,257,275 | 6/1966 | Weisberg et al. | 514/55 |
| 3,879,376 | 4/1975 | Vanlerberghe | 536/20 |
| 3,969,498 | 7/1976 | Catania et al. | 424/DIG. 13 |
| 4,386,151 | 5/1983 | Berger et al. | 430/228 |
| 4,391,799 | 7/1983 | Mason et al. | 424/132 |
| 4,393,048 | 7/1983 | Mason et al. | 424/132 |
| 4,528,283 | 7/1985 | Lang et al. | 514/55 |

FOREIGN PATENT DOCUMENTS

| | | | |
|---|---|---|---|
| 0047479 | 4/1978 | Japan | 536/20 |
| 0139310 | 8/1984 | Japan | 514/55 |
| 2107340 | 4/1983 | United Kingdom | 536/20 |

OTHER PUBLICATIONS

Pittalis et al., Hollow Chitosan Fibers, Chem. Abstracts 99:39744q (1983).

Shiseido Co., Ltd., Emulsions Containing Alginates, Polyalcohols and Oils, Chem. Abstracts 100:12461x (1983).

*Primary Examiner*—Johnnie R. Brown

[57] ABSTRACT

A chitosan-glycerol-water gel or gel-like membrane, useful as a carrier for medicaments to be applied to wounds, is prepared by dissolving chitosan in an acid-water-glycerol solution, which when neutralized, forms a gel upon standing.

5 Claims, No Drawings

CHITOSAN-GLYCEROL-WATER GEL

This invention relates to a chitosan carrier in wound care and to a process for its formation from a solution of chitosan in a glycerol-water-acid solution by neutralizing said chitosan solution.

BACKGROUND OF THE INVENTION

For application of various substances to wounds, it is desirable to find a carrier material which is relatively inexpensive, is easily applied to the wound, is a good carrier for medicaments to be applied to the wound, is biodegradable, and is relatively free from any adverse effect on the various aspects of the complex wound healing process. The chitosan gel of the present invention meets these stringent requirements. The chitosan gel may also be obtained and used in the form of a gel-like membrane for the purposes of the present invention.

Chitosan is a relatively inexpensive commercially available material. It is derived from chitin, an insoluble linear polymer of N-acetylglucosamine, found in the hard shells of crustaceans e.g., shrimp, lobster, crab, which are treated to remove extraneous material.

Chitosan is derived from chitin by removal of a proportion of the N-acetyl groups which renders it soluble in many acids, including certain dilute organic acids, such as formic, acetic and propionic acids. Both chitin and chitosan have been used for a variety of purposes, usually as powders, in solution or membranes in the form of viscoses analogous to cellulose viscose. However, these forms are not readily usable for the purpose described above.

SUMMARY OF THE INVENTION

It has now been found that a gel, or gel-like membrane, which meets the above requirements for use on wounds can be easily made from chitosan dissolved in an acid-water-glycerol solution which is then neutralized with a base. The resultant neutral solution unexpectedly turns into a gel upon standing. If a thin layer of the acid-water-glycerol-chitosan solution is used, upon neutralization, a gel-like membrane is formed.

The chitosan starting material is preferably used in finely powdered form, so that it will dissolve easier in the solvent solution. The concentration of chitosan can be about 1-4%, with 1% being preferred.

The acid to be used in the solvent solution can be any pharmaceutically acceptable acid in which chitosan is soluble, with the preferred acids being acetic, formic and propionic acid, and acetic acid the most preferred.

The glycerol (1,2,3-propanetriol) which is used can be present in a wide range or proportion of 10-90% of the acid-water-glycerol solution, but to obtain good gel-like consistency requires that a concentration of at least 50% of glycerol be used. Thus the lesser proportions of glycerol are useful when a gel-like membrane is desired, but if at least 50% glycerol is used either a gel or a gel-like membrane can be obtained.

The base which is used to neutralize the acid-glycerol-water-chitosan solution can be any pharmaceutically acceptable base, e.g., sodium hydroxide, ammonium hydroxide or potassium hydroxide ammonia are typical and illustrative of suitable bases. However, NaOH is the preferred base when a gel is desired. When a gel-like membrane is desired, exposure to ammonia vapor is preferred.

The chitosan-containing gels or gel-like membranes of the present invention are excellent carriers for various medicaments, such as antibacterial agents e.g., silver sulfadiazine, quaterary ammonium agents, iodophors, vasodilators such as epinephrine, ketanserin, compounds which promote wound healing, analgesics, anti-inflammatory agents and the many other medicaments which are customarily applied to wounds in such a manner. The gels apparently remain relatively stable and retain their three dimensional structures for long periods of time over wide variation in temperature e.g., from 4° to 40° C., and are suitable for pharmaceutical use. They can be sterilized by irradiation.

The following examples are intended to illustrate, but not to limit, the present invention.

EXAMPLE 1—CHITOSAN-GLYCEROL-ACETIC ACID-GEL

1% glacial acetic acid solution and glycerol was mixed in a ratio of 1 part of said acetic acid solution to 3 parts of glycerol to form a solvent. One gram (1 g) chitosan (in finely powdered form) was dissolved in 100 ml of the aforesaid solvent by stirring with a magnetic stirrer at room temperature for 1-2 hours to form a clear pale yellow solution. The solution was neutralized by adding 5N NaOH until pH 7 was reached. Immediately a clear slightly tacky gel formed. The gel, which apparently results from the interaction of chitosan, glycerol and water, has a three dimensional structure, and no free water or glycerol is apparent.

EXAMPLE 2—CHITOSAN-GYCEROL-ACETIC ACID-GEL-LIKE MEMBRANE

Following the procedure described in Example 1 the clear pale yellow solution of chitosan was poured into a petri dish to form a thin layer. The thin layer was neutralized by exposure to ammonia vapor, thereby forming a clear gel-like membrane.

EXAMPLE 3—ADDITION OF MEDICAMENT

The gel of Example 1 and the gel-like membrane of Example 2 are excellent carriers for any medicament which is customarily administered in those forms e.g., antibacterial agents, e.g., silver sulfadiazine, quaterary ammonium agents, iodophors, vasodilators such as epinephrine, ketanserin, compounds which promote wound healing, analgesics, anti-inflammatory agents and the like. These medicaments can be added to the acid-water-glycerol-chitosan solution prior to neutralization with the base. Thus if 10% povidone-iodine is added to the acid-water glycerol solution of chitosan of Example 1 or Example 2 before neutralization with the base, the gel or gel-like membrane which is obtained upon neutralization will have the antibacterial properties of a 10% povidone iodine preparation.

The chitosan gel of Example 1 was tested for its effect on wound healing by being placed on excised wounds in guinea pigs, which were then covered with an occlusive dressing and an adhesive bandage. The wound was examined at 5 and 8 days with the following results: Normal healing occurred with no sign of cytotoxicity or inflammation.

What is claimed is:

1. A gel or gel-like membrane consisting essentially of water, chitosan and glycerol, and having a 3-dimensional gel structure.

2. The gel of claim 1, in a clear form and wherein the amount of chitosan present is from 1-4%, the amount of glycerol present is 50-90%, and the pH of the gel is about pH 7.

3. The gel of claim 2, which also contains a medicament.

4. The gel-like membrane of claim 1, in a clear form and wherein the amount of chitosan present is from 1-4%, the amount of glycerol present is 10-90%, and the pH of the gel-like membrane is about pH 7.

5. The gel-like membrane of claim 4, which also contains a medicament.

* * * * *